(12) United States Patent
Keller et al.

(10) Patent No.: US 8,199,021 B2
(45) Date of Patent: *Jun. 12, 2012

(54) FLUID LEVEL DETECTION SYSTEM

(75) Inventors: Robert D. Keller, Davisburg, MI (US); William G. Spurrier, III, Macomb Township, MI (US); Gerrit V. Beneker, Lake Orion, MI (US); Jeffrey B. Smith, Rochester Hills, MI (US); Mark L. Dell'Eva, Grand Blanc, MI (US)

(73) Assignee: Eaton Corporation, Cleveland, OH (US)

(*) Notice: Subject to any disclaimer, the term of this patent is extended or adjusted under 35 U.S.C. 154(b) by 405 days.

This patent is subject to a terminal disclaimer.

(21) Appl. No.: 12/506,653

(22) Filed: Jul. 21, 2009

(65) Prior Publication Data

US 2011/0018723 A1 Jan. 27, 2011

(51) Int. Cl.
*G08B 21/00* (2006.01)
(52) U.S. Cl. ..................................... 340/603; 73/114.55
(58) Field of Classification Search .................. 340/603, 340/450.3; 73/53.05, 54.23, 54.25, 54.26, 73/54.37, 114.55, 114.56
See application file for complete search history.

(56) References Cited

U.S. PATENT DOCUMENTS

| | | | |
|---|---|---|---|
| 2,285,255 A * | 6/1942 | Davis | 73/53.05 |
| 4,583,085 A | 4/1986 | Beller | |
| 4,762,000 A | 8/1988 | Bond, Jr. | |
| 7,921,703 B2 * | 4/2011 | Keller et al. | 73/114.55 |
| 2005/0212533 A1 | 9/2005 | Itomi | |
| 2008/0093172 A1 | 4/2008 | Albertson | |
| 2008/0250851 A1 | 10/2008 | Keller | |
| 2010/0281971 A1 * | 11/2010 | Beneker et al. | 73/290 R |

FOREIGN PATENT DOCUMENTS

| | | |
|---|---|---|
| DE | 4125588 A1 | 2/1993 |
| DE | 19902991 C1 | 7/2000 |
| DE | 10242959 A1 | 11/2003 |
| WO | 8603297 | 6/1986 |
| WO | 9113322 | 9/1991 |

* cited by examiner

*Primary Examiner* — John A Tweel, Jr.
(74) *Attorney, Agent, or Firm* — Quinn Law Group, PLLC

(57) ABSTRACT

A fluid level detection system includes a fluid reservoir defining a cavity for holding fluid therein. A fluid level sensor is mounted to the fluid reservoir. The solenoid body defines a first opening establishing fluid communication between an armature chamber and a cavity defined by the reservoir. Travel time of an armature within the armature chamber is thereby affected by fluid level in the reservoir. A controller is operatively connected to the sensor and is operable to receive a sensor signal indicative of travel time from the sensor and formulate a control signal corresponding thereto. A power source is operatively connected to the controller for energizing the coil and the controller. In some embodiments, multiple fluid containing components are connected with one or more controllers. An engine, a transmission, and rear axle differentials on a vehicle may be equipped with sensors to provide fluid level, temperature and viscosity information.

20 Claims, 5 Drawing Sheets

FLUID LEVEL DETECTION SYSTEM

TECHNICAL FIELD

The invention relates to a system for detecting fluid level in a reservoir, and includes a fluid level sensor and a controller.

BACKGROUND OF THE INVENTION

In a variety of systems that contain and utilize fluid for pressure, lubrication, or otherwise, it is important to maintain fluid at an appropriate level in order to ensure proper functioning of system components. For example, fluid-containing components on vehicles, such as engines, transmissions, and differentials, must be kept lubricated for cooling or torque-transmission purposes. It is important that operating fluid levels are monitored.

SUMMARY OF THE INVENTION

A fluid level detection system is provided that includes a fluid reservoir defining a cavity for holding fluid therein. A fluid level sensor having a solenoid body is mounted to the fluid reservoir and has a first portion extending inside of the cavity and a second portion extending outside of the reservoir. The portion extending outside of the reservoir may be only electrical connectors, or may be more of the solenoid body. The sensor also has a coil, an armature, a pole piece, and a biasing device biasing the armature away from the pole piece. The biasing device and coil are configured to cycle the armature in the armature chamber as the coil is cyclically energized. The solenoid body defines an armature chamber in which the armature travels in response to energizing of the coil. The solenoid body defines a first opening establishing fluid communication between the armature chamber and the cavity defined by the reservoir. Travel time of the armature within the armature chamber is thereby affected by fluid level in the reservoir.

The sensor is operable to provide a sensor signal indicative of the travel time. A controller is operatively connected to the sensor and is operable to receive the sensor signal from the sensor and formulate a control signal corresponding thereto. A power source is operatively connected to the controller for energizing the coil and the controller.

In some embodiments, multiple fluid containing components are connected with one or more controllers to provide a control signal indicative of fluid level, temperature and/or viscosity in the components to the output device. For example, an engine, a transmission, and rear axle differentials on a vehicle may be equipped with sensors to provide fluid level, temperature and viscosity information to a vehicle operator.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

First Embodiment of a Fluid Level Detection System

Figure 1:
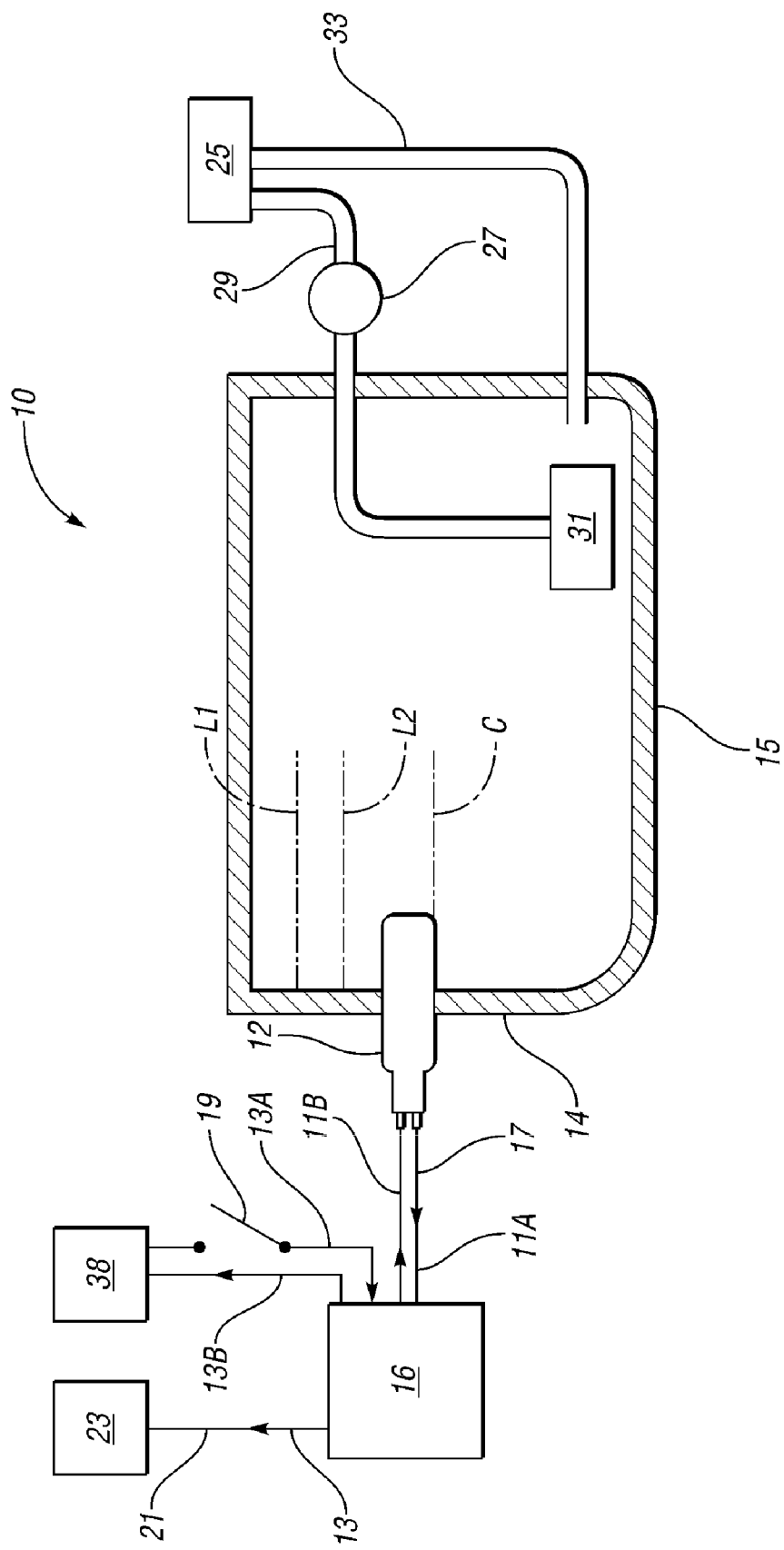
FIG. 1 is a schematic illustration of a first embodiment of a fluid level detection system with a fluid reservoir in fluid communication with a fluid-requiring component.

Referring to the drawings, wherein like reference numbers refer to like components throughout the several views, FIG. 1 shows a fluid level detection system 10 that includes a fluid level sensor 12 mounted to a wall 14 of a fluid reservoir 15 or fluid containing component for sensing fluid level L therewithin. The sensor 12 is described in more detail below with respect to FIG. 5. An alternative embodiment of a sensor 112 that may be used in place of sensor 12 is shown in FIG. 6. In describing FIG. 1, reference will be made to fluid reservoir 15. However, the fluid reservoir 15 could instead be a fluid-containing component, such as engine 15E, transmission 15F, first axle differential 15G or second axle differential 15H of FIG. 4A. Alternatively, the fluid reservoir 15 may be in a nonautomotive environment, such as the food processing industry, in which large fluid-containing vats are often used to mix, heat, or otherwise process food and drinks. The fluid reservoir 15 may be used in any industry in which the ability to track the level of stored fluid is important. The sensor 12 is secured to the reservoir 15 so that the fluid condition and level sensor 12 is positioned in the reservoir 15 to enable detection of multiple fluid conditions, including fluid temperature, fluid viscosity, a full fluid level, and a low fluid level, as further described herein.

As described below with respect to FIG. 1, the sensor 12 is operable for providing a sensor signal 17 to an electronic controller 16 via a first cable 11A or wirelessly. The controller 16 may be positioned inside of or outside of the reservoir 15. The sensor signal 17 is indicative of fluid level in the reservoir 15. The sensor signal from the sensor 12 may also be indicative of fluid temperature and fluid viscosity. An ignition switch 19 may be closed to provide electric current along transfer conductor 13A from a power source 38, such as a battery, generator, or solar cell, to the controller 16, which in turn energizes the sensor 12, via conductor 11B, as described below with respect to FIG. 5. The conductor 11B may be bundled in a cable with first cable 11A. The controller 16 communicates with the power source 38 via a transfer conductor 13B. The controller 16 has a processor on which is stored an algorithm that compares the sensor signal 17 to stored values in a look-up table to determine fluid level (and/or temperature and viscosity) of fluid in the reservoir 15. The controller 16 then provides a control signal 21 along a transfer conductor to an output device 23 via a second cable 13 or wirelessly. Alternatively, the controller 16 may communicate with the output device 23 and the sensor 12 wirelessly. The output device 23 may provide a visual indicator or an audio indicator of the fluid level, temperature or viscosity. For example, the visual indicator may be a light indicating a low level of fluid. The audio indicator may be an alarm indicating low fluid level.

In embodiments where the reservoir 15 is a fluid reservoir in fluid communication with a fluid-requiring component 25, such as an engine, a food processing machine, etc., a pump 27 provides fluid directed through a filter 31 to the component 25 via conduit 29 when the component 25 is in an "on" state (i.e., is operating and in need of fluid), and does not provide fluid when the component 25 is in an "off" state (i.e., is not in need of fluid). The fluid is eventually returned to the reservoir 15 via conduit 33. Thus, when the component 25 is in the off state, fluid in the reservoir will be at a static level L1, but will be drawn down to a dynamic level L2 when the component 25 is in the on state. The sensor 12 is operable, as described below, to indicate the fluid level and monitor when the fluid level goes below a critical level, such as if the dynamic level L2 drops below level C corresponding with an opening 64 in the sensor 12, shown in FIG. 5.

First Embodiment of a Fluid Level Sensor

Figure 5:
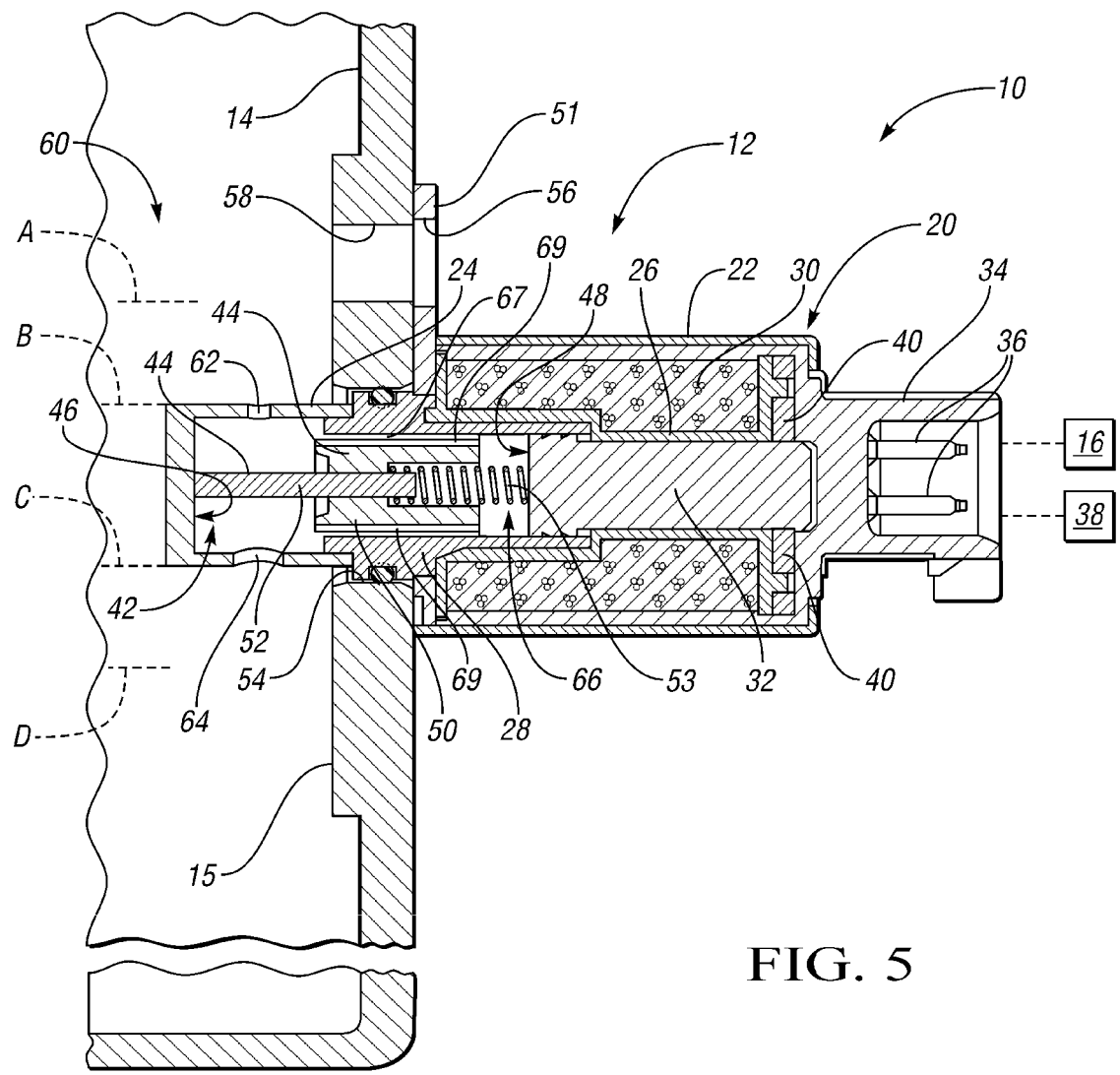
FIG. 5 is a cross-sectional illustration of a first embodiment of a fluid level sensor for use in the fluid level detection systems of FIGS. 1-4B.
Figure 6:
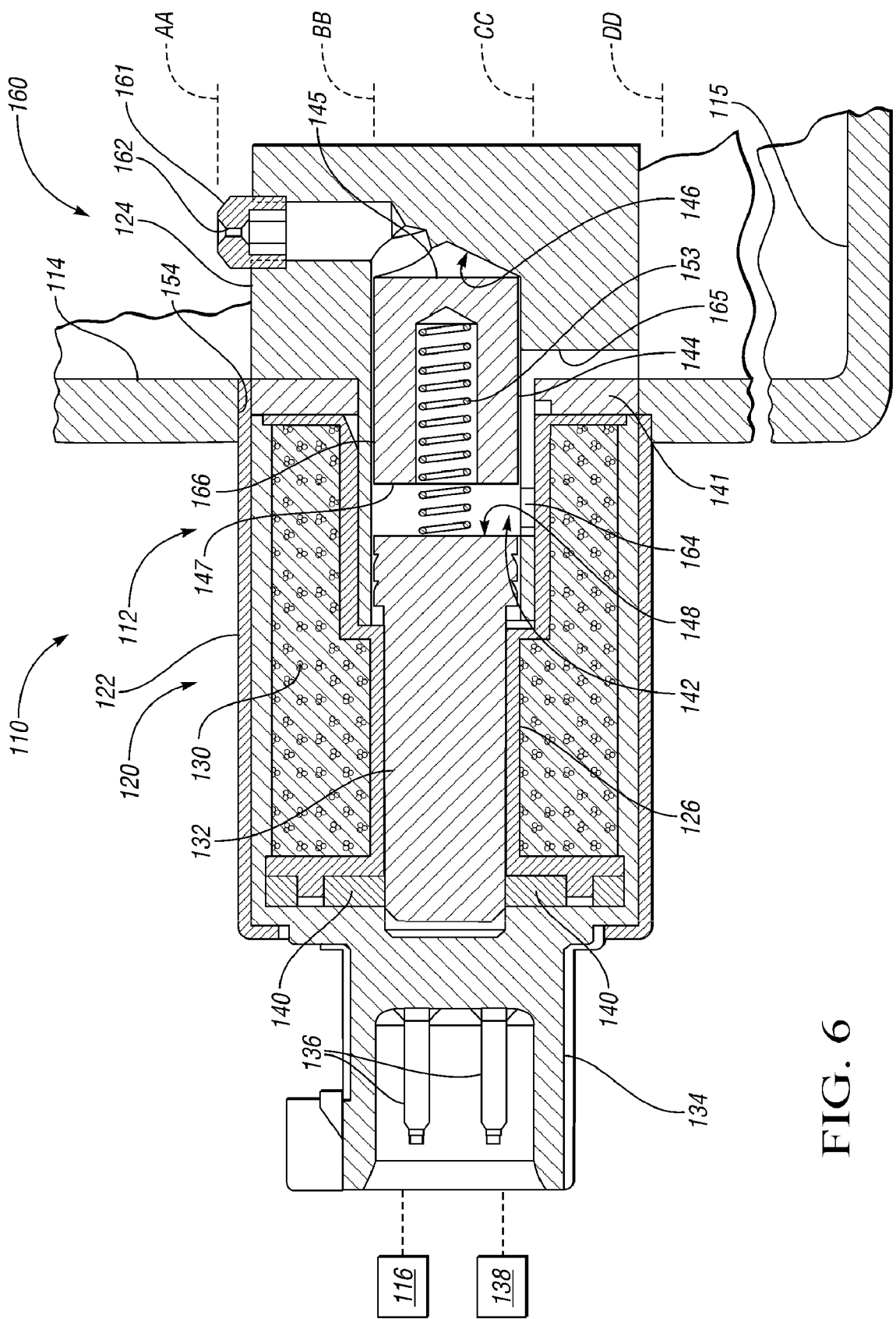
FIG. 6 is a cross-sectional illustration of a second embodiment of a fluid level sensor for use in the fluid level detection systems of FIGS. 1-4B.

Referring to FIGS. 5 and 6, the structure and operation of two alternative fluid level sensors 12 and 112 is described in detail. Referring to FIG. 5, the fluid condition and level sensor 12 has a solenoid body 20 that includes an outer portion 22, also referred to as a can, a base portion 24, a coil support portion 26, an extension portion 28 and a cap portion 34. The coil support portion 26 (also referred to as a bobbin) supports a coil 30. The outer portion 22, base portion 24, coil support portion 26, extension portion 28, and cap portion 34 may be made integral or made unitary with one another by casting, molding, or other processes.

A pole piece 32 is press-fit or otherwise secured within the outer portion 22. The cap portion 34 surrounds a distal end of the pole piece 32 and has an electrical connector 36 therethrough operatively connected to a power source 38, such as a battery, and to the controller 16. Flux collectors 40 are positioned between the pole piece 32 and the cap portion 34.

The base portion 24 and extension portion 28 of the solenoid body 20, along with the pole piece 32, define an armature chamber 42 in which an armature 44 travels between an end surface 46 of the base portion 24 and an end surface 48 of the pole piece 32. The armature 44 includes a body portion 50 and a rod portion 52 extending therefrom. A biasing device, such as spring 53, is positioned between the pole piece 32 and the armature body portion 50 to bias the armature 44 away from the pole piece 32 to the unenergized position shown (i.e., the position of the armature 44 when the coil 30 is not energized).

A mounting flange 51 secures the sensor 12 through an opening 54 in the reservoir side wall 14. A bolt or other fastening mechanism (not shown) extends through mating openings 56, 58 of the flange 51 and the side wall 14. When secured to the reservoir 15, the base portion 24 extends into a cavity 60 defined by the reservoir 15. The remainder of the sensor 12 is external to the reservoir 15. The base portion 24 has an upper opening 62 and a lower opening 64. As used herein, upper opening 62 is referred to as the first opening.

The armature 44 travels generally transverse to a direction of fluid level change in the reservoir 15. That is, the armature 44 travels back and forth in the armature chamber 42 generally transverse (perpendicular) to the direction of decreasing fluid level (from level A, to level B, to level C, to level D), or increasing fluid level (from level D, to level C, to level B, and to level A). The sensor 12 may alternatively be mounted so that the armature travels at a different angle with respect to fluid in the reservoir 15.

The pole piece 32, outer portion 22, coil 30, flux collectors 40, flange 51 and armature 44 form an electromagnet. Lines of flux are created in a gap 66 between the pole piece 32 and the armature 44 when the coil 30 is energized by the electric source 38. When the coil 30 is energized, the magnetic flux drives the armature 44 toward the pole piece 32, decreasing the portion of the armature chamber 42 between end surface 48 and the armature 44. When energy to the coil 30 ceases, the spring 53 drives the armature 44 back to the unenergized position shown, increasing the portion of the armature chamber 44 between surface 48 and armature 44. Fluid, whether air or liquid, is pushed through the openings 62, 64 as the armature 44 travels. Fluid in the gap 66 of the armature chamber 42 is also forced through a clearance 67 between the outer diameter of the armature 44 and the inner diameter of the extension portion 28 as the armature 44 is cycled. Fluid is similarly forced through channels 69 in the armature 44. The clearance 67 and channels 69 are configured to be more resistant to fluid flow than the openings 62, 64. Thus, armature travel time is a function of the resistance to fluid flow through clearance 67 and channels 69, which in turn is dependent on whether air or liquid is present in the chamber 42 and forced through the clearance 67 and channels 69.

The solenoid valve 20 has a distinctive inductive kick, which is a distinct dip in current draw followed by an increase in current draw indicative of the armature 44 reaching the end of travel under known fluid temperature and fluid fill level. The time period to an inductive kick after the solenoid valve 20 is energized, is thereby affected by the resistance to travel encountered by the armature 44. The inductive kick phenomena of solenoid valves is well understood by those skilled in the art, and is shown and described in commonly owned United States Patent Application Publication No. 20080250851A1, published Oct. 16, 2008, which is hereby incorporated by reference in its entirety.

The chamber 42, clearance 67, channels 69, and openings 62, 64 described above establish armature travel times indicative of various fluid conditions such as fluid viscosity and a fluid change occurrence, as well as various fluid levels in the reservoir 15, as described below. By tracking the time until the inductive kick, and comparing the time with predetermined times in a look-up table stored on the controller 16, the controller 16 is able to determine liquid level and viscosity. The sensor 12 is also operable to determine oil temperature based on current.

Fluid Viscosity

When the coil 30 is energized and deenergized, the armature 44 moves within the chamber 42. When the armature 44 moves away from the pole piece 32, fluid is also pushed through clearance 67 and channels 69 from chamber 42. By summing the total resistance to fluid flow through the clearance 67 and channels 69 and friction of the moving parts, this slows the armature movement such that by measuring the time of armature motion and then applying an algorithm stored in controller 16, the response time corresponds to a value indicating the viscosity of the fluid. A higher fluid viscosity causes the armature 44 to move more slowly as it is cycled, increasing the armature response time. The inductive kick that occurs at the end of the armature travel in the cycle is detected by the controller 16, which is connected to coil 30. The thicker the fluid, the longer it will take for the inductive kick to occur. The total armature response time is then checked in a look-up table stored in the controller 16 to obtain the relative viscosity of the fluid. Fluid viscosity can thus be measured using the sensor 12, except when liquid fluid level is at an extreme low level (i.e., below opening 64, such as at level D).

The resistance of the sensor 12 may also be measured and the engine controller voltage controlled to maintain a constant operating current to the sensor 12 and thus a constant force of the armature 44. This reduces any effects of current variability on the armature response time. Limiting the voltage below 12 volts can slow the armature 44 even further to modify the response time versus viscosity relationship and thereby increase the sensor sensitivity.

Fluid Level

When liquid fluid within the reservoir 15 is above a predetermined full level B, such as at level A, armature travel time is a function of the sum of the resistances to fluid travel through the clearance 67 and the channels 69, with viscous drag on the armature 44 also having a slight effect. The openings 62, 64 are sized large enough to permit fluid flow therethrough relatively freely, so that flow through the clearance 67 and channels 69 determines armature travel time. Because these resistances will vary as liquid fluid level varies, the fluid condition system 10 can monitor and record liquid fluid level within the reservoir 15, recognizing the instant current liquid level as being within one of two ranges: above a first level (full level B), and below a second level (low level C). This information can be conveyed to a system operator, such as a vehicle driver, if desired, by connecting an output device 23 (see FIG. 1), such as a display monitor on an instrument panel screen, to the controller 16 and programming the controller 16 to send a control signal 21 to the monitor corresponding to the monitored fluid level.

If liquid level in the pan 15 is at any level below the opening 64 (i.e., below level C), as indicated by "excessive low" fluid level D in FIG. 5, any fluid in the chamber 42 is forced out of openings 62, 64 on the first armature cycle. When the armature 44 cycles, air is drawn into the chamber 42 instead of liquid, since the openings 62, 64 are above the liquid level. On subsequent cycles, because only air is moving through the openings 62, 64, clearance 67, and channels 69, the armature movement time is relatively fast. Thus, the controller 16 will recognize such an armature travel time as indicative of an "excessive low" liquid fluid level, will store this information, and may be programmed to send a notification to a display in order to notify the vehicle operator of the need to add fluid.

When liquid fluid is at any level above the opening 62 (i.e., above level B), the chamber 42 will be constantly filled with liquid as the armature 44 travels, and liquid will be forced through the clearance 67 and channels 69. This will create a unique armature travel time recognized by the controller 16 as indicative of a full liquid fluid level, and being a function of the sum of resistances to fluid flow through clearance 67 and channels 69. The sensor 12 may be mounted to the reservoir 15 such that level B represents a minimum desired static liquid level and level C represents a minimum desired dynamic liquid level.

Fluid Temperature

The temperature of the coil 30 will be affected by the fluid. To measure fluid temperature, the coil resistance is measured and then checked against a temperature look-up table stored within the controller to determine the temperature of the fluid. Alternatively, the sensor 12 may be cycled with a predefined voltage. By measuring the current, the coil resistance can be calculated and then correlated with temperature.

Second Embodiment of a Fluid Level Sensor

Referring to FIG. 6, another embodiment of a fluid condition and level sensing system 110 including a fluid condition and level sensor 112 extending through a side wall 114 of a reservoir 115. The sensor 112 is secured to the reservoir 115, such as an engine oil pan on a vehicle, so that the fluid condition and level sensor 112 is positioned in a cavity 160 defined by the reservoir 115 to enable detection of multiple fluid conditions, including fluid temperature, fluid viscosity, and multiple fluid levels, as further described herein. The fluid condition and level sensor 112 is operatively connected to an electronic controller 116, which may be contained either inside or outside of the reservoir 115, such as on a vehicle engine or elsewhere in the vehicle.

Referring to FIG. 6, the fluid condition and level sensor 112 has a solenoid body 120 that includes an outer portion 122, also referred to as a can, a base portion 124, a coil support portion 126, and a cap portion 134. The coil support portion 126 (also referred to as a bobbin) supports a coil 130. The outer portion 122, base portion 124, coil support portion 126, and cap portion 134 may be made integral or made unitary with one another by casting, molding, or other processes.

A pole piece 132 is press-fit or otherwise secured within the outer portion 122. The cap portion 134 surrounds a distal end of the pole piece 132 and has an electrical connector 136 therethrough operatively connected to a power source 138, such as a battery, and to the controller 116. Flux collectors 140 are positioned between the pole piece 132 and the cap portion 134. A washer 141 is positioned between the coil support portion 126 and the base portion 124.

The base portion 124 of the solenoid body 120, along with the pole piece 132, define an armature chamber 142 in which an armature 144 travels between an unenergized position shown (near an end surface 146 of the base portion 124) and an energized position (closer to an end surface 148 of the pole piece 132). A biasing device, such as spring 153, is positioned between the pole piece 132 and the armature 144 to bias the armature 144 away from the pole piece 132 to the unenergized position shown (i.e., the position of the armature 144 when the coil 130 is not energized).

A mounting flange (not shown) secures the sensor 112 through an opening 154 in the reservoir side wall 114. A bolt or other fastening mechanism (not shown) extends through mating openings of the flange and the side wall 114. When secured to the reservoir 115, the base portion 124 extends into a cavity 160 defined by the reservoir 115. The remainder of the sensor 112 is external to the reservoir 115.

The base portion 124 has an extension 161 with an upper opening 162 and a lower opening 164. As used herein, upper opening 162 is referred to as the first opening. As best shown in FIG. 6, the lower opening 164 extends axially and is in communication with a radial slot 165.

In this embodiment, the armature 144 travels generally transverse to a direction of fluid level change in the reservoir 115. That is, the armature 144 travels back and forth in the armature chamber 142 generally transverse (perpendicular) to the direction of decreasing liquid fluid level from level AA, to level BB to level CC, to level DD, or increasing liquid fluid level change from level DD, to level CC, to level BB, and to level AA. The sensor may alternatively be positioned so that the armature travels at other angles with respect to the fluid level.

The pole piece 132, outer portion 122, coil 130, flux collectors 140, washer 141 and armature 144 form an electromagnet. Magnetic flux is created when the coil 130 is energized by the electric source 138. The magnetic flux drives the armature 144 toward the pole piece 132, increasing the portion of the armature chamber 142 between end surface 146 and the side 145 of the armature 144. When energy to the coil 130 ceases, the spring 153 drives the armature 144 back to the unenergized position shown, decreasing the portion of the armature chamber 142 between surface 146 and armature 144. Fluid, whether air or liquid, such as oil, is pushed through the openings 162, 164 as the armature 144 travels. Opening 162 communicates air or liquid with the chamber 142 at a first side 145 of the armature 144. Opening 164 communicates air or liquid within the reservoir 115 below level DD with a second side 147 of the armature 144. Air can be communicated between the portions of the chamber 142 at the two sides 145, 147 of the armature 144 through a clearance 166 between the inner diameter of the cavity forming the chamber 142, and the outer diameter of the armature 144. The clearance 166 is designed to inhibit any communication of liquid therethrough. Thus, armature travel time is a function of the resistance to fluid flow through the openings 162, 164, which in turn is dependent on whether air or liquid is flowing through the openings. The time period to an inductive kick after the solenoid 120 is energized, is thereby affected by the resistance to fluid flow through the openings 162, 164. The chamber 142 and openings 162, 164 described above establish armature travel times indicative of various fluid conditions such as fluid viscosity and a fluid change occurrence, as well as various fluid levels in the reservoir 115, as described below. By tracking the time until inductive kick, and comparing the time with predetermined times in a look-up table stored on the controller 116, the controller 116 is able to determine liquid fluid level and viscosity. The sensor 112 is also operable to determine fluid temperature based on current.

Fluid Viscosity

When the coil 130 is cycled (energized and deenergized), the armature 144 moves back and forth within the chamber 142. When the coil 130 is energized and deenergized, the armature 144 moves toward and away from the pole piece 132, respectively, and fluid is pushed through openings 162, 164 from chamber 142. The total resistance to fluid flow of the openings 162, 164 and friction of the moving parts slows the armature movement such that by measuring the time of armature motion and then applying an algorithm stored in the controller 116, the response time corresponds to a value indicating the viscosity of the fluid. A higher fluid viscosity causes the armature 144 to move more slowly as it is cycled, increasing the armature response time. The inductive kick that occurs at the end of the armature travel toward the pole piece 132 is detected by the controller 116, which is connected to coil 130. The thicker the fluid, the longer it will take for the inductive kick to occur. The total armature response time is then checked in a look-up table stored in the controller 116 to obtain the relative viscosity of the fluid. Fluid viscosity can thus be measured using the sensor 112 (except when fluid is at an extreme low level (i.e., below opening 164, such as at level D).

The resistance of the sensor 112 may also be measured and the engine controller voltage controlled to maintain a constant operating current to the sensor 112 and thus a constant force of the armature 144. This reduces any effects of current variability on the armature response time. Limiting the voltage below 12 volts can slow the armature 144 even further to modify the response time versus viscosity relationship and thereby increase the sensor sensitivity.

Fluid Level

When liquid within the reservoir 115 is above a predetermined full level AA, armature travel time is a function of the sum of the resistances to fluid travel through each of the openings 162, 164, with viscous drag on the armature 144 also having a slight effect. Because these resistances will vary as liquid fluid level varies, the fluid condition system 110 can monitor and record fluid level within the reservoir 115, recognizing the current liquid fluid level as being within one of three ranges: above level AA (e.g., an overfill level), below level DD (e.g., a low level), and between level AA and level DD (e.g., a full level). This information can be conveyed to a vehicle operator, if desired, by connecting an output device 23 (see FIG. 1) such as a display monitor, such as on an instrument panel screen, to the controller 116 and programming the controller 116 to send a control signal to the monitor corresponding to the monitored liquid fluid level.

If fluid level in the reservoir 115 is at any level below the opening 164, (i.e., any level below level DD in FIG. 1), any liquid fluid in the chamber 142 is forced out on the first armature cycle. When the armature 144 cycles, air is drawn into the chamber 142 instead of liquid, since the openings 162, 164 are above the liquid fluid level. On subsequent cycles, because only air is moving through the openings 162, 164, the armature movement time is relatively fast. Thus, the controller 116 will recognize such an armature travel time as indicative of an "excessive low" liquid fluid level, will store this information, and may be programmed to send to a display a notification to the system operator of the need to add oil.

If liquid fluid level in the pan 115 is at any level below the opening 162, but above the opening 164 (i.e., a level between level AA and level DD, such as level BB and level CC), the armature 144 will displace at least some liquid fluid out of the chamber 142 on the first armature cycle. When the spring 153 biases the armature 144, opening 164 will draw in fluid. Because opening 162 is above the liquid fluid level, and at least some of the chamber 142 is above liquid fluid level, some air will be drawn into the chamber 142 when the sensor 112 is energized. Therefore, the armature movement time will be slower than when liquid fluid is at the extreme low level DD, but not as slow as when fluid level is above opening 162. The controller 116 will compare the armature movement time to stored values and recognize such an armature travel time as indicative of a level between level AA and level DD.

When liquid fluid is at any level above the opening 162, such as above level AA, the chamber 142 will be constantly filled with liquid fluid as the armature 144 travels, and liquid will be forced through openings 162, 164. This will create a unique armature travel time recognized by the controller 16 such as indicative of an overfill level, depending on the mounted position of the sensor 112 within the reservoir 115, and being a function of the sum of resistances to fluid flow through openings 162, 164.

Fluid Temperature

The temperature of the coil 130 will be affected by the fluid. To measure fluid temperature, the coil resistance is measured and then checked against a temperature look-up table stored within the controller to determine the temperature of the fluid. Alternatively, the sensor 112 may be cycled with a predefined voltage. By measuring the current, the coil resistance can be calculated and then correlated with temperature.

Second Embodiment of a Fluid Level Detection System

Figure 2:
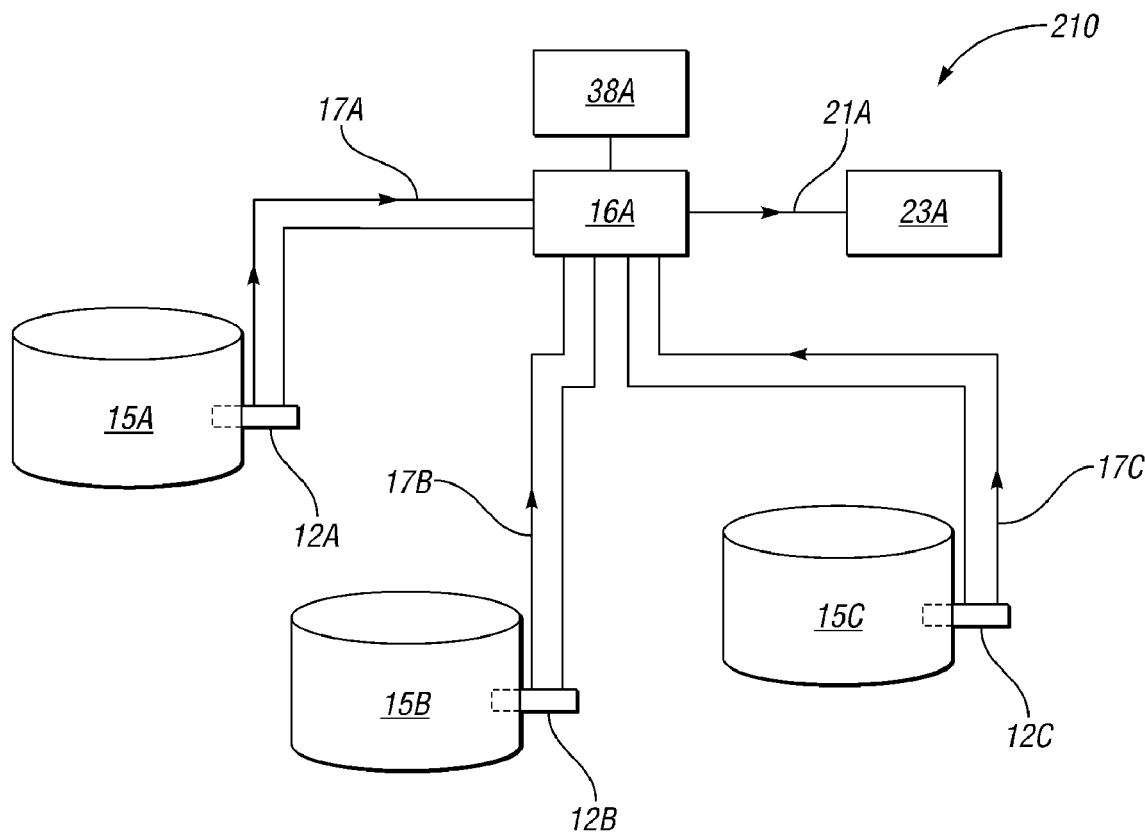
FIG. 2 is a schematic illustration of a second embodiment of a fluid level detection system with multiple fluid reservoirs.

Referring to FIG. 2, a fluid level detection system 210 has multiple fluid-containing reservoirs 15A, 15B, 15C, such as may be used in a processing system utilizing fluid or fluids. Each reservoir 15A, 15B, 15C has a fluid condition and level sensor 12A, 12B, 12C, respectively, mounted thereto and operable as described above. Each sensor 12A, 12B, 12C communicates a separate sensor signal 17A, 17B, 17C along transfer conductor wires, or wirelessly, to a system controller 16A configured to process each of the sensor signals and provide a control signal 21A providing level, temperature and/or viscosity information for each reservoir 15A, 15B, 15C to an output device 23A to enable monitoring of the reservoirs 15A, 15B, 5C. Although three reservoirs 15A, 15B, 15C are shown, the system 210 may have from one to hundreds or more reservoirs. A power source 38A which may be a battery, a generator, a solar cell or other form of power is operatively connected to the controller 16A for providing power to the controller 16A and through the controller 16A to the sensors 12A, 12B, 12C for energizing the sensors 12A, 12B, 12C. The transfer conductors shown providing the sensor signals 17A, 17B, 17C and providing power from the controller 16A to the sensors 12 may be bundled in a unitary bus or otherwise, if the relative positions of the reservoirs 15A, 15B, 15C permit.

Third Embodiment of a Fluid Level Detection System

Figure 3:
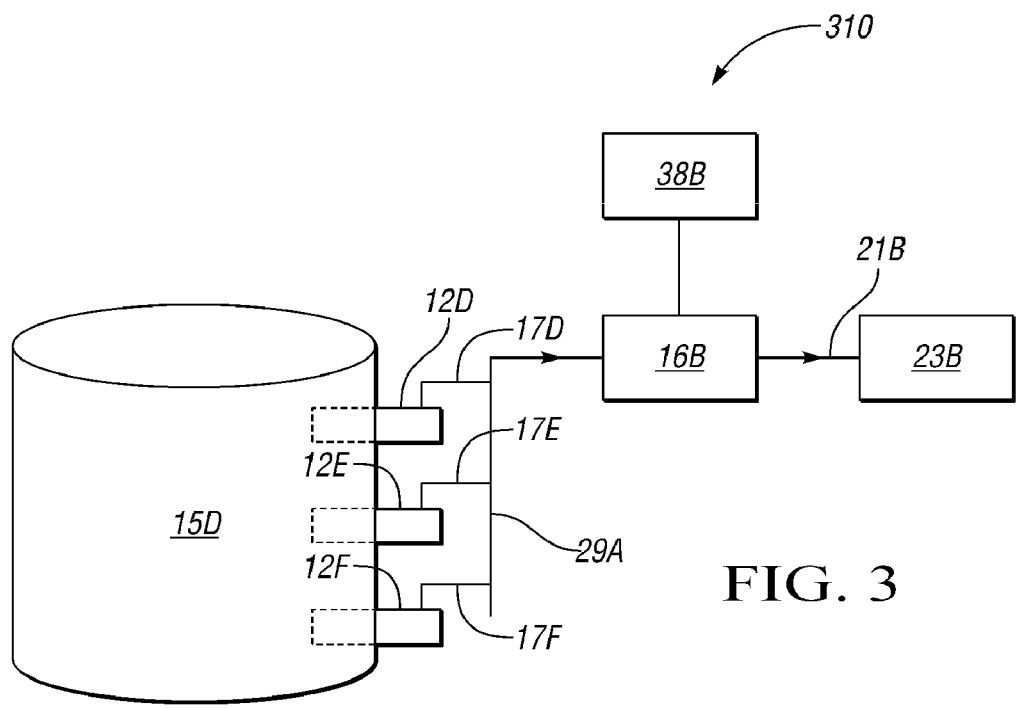
FIG. 3 is a schematic illustration of a third embodiment of a fluid level detection system with multiple fluid level sensors at different locations on a fluid reservoir.

Referring to FIG. 3, a fluid level detection system 310 has a single reservoir 15D with three fluid condition and level sensors 12D, 12E, 12F identical to one another and identical to sensor 12, or alternatively sensor 112, described above, but mounted at different locations on the reservoir 15D. Sensor 12D is mounted at a first location, sensor 12E is mounted at a second location lower than the first location, and sensor 12F is mounted at a third location lower than either of the other locations. Thus, each sensor 12D, 12E, 12F is operable for providing a different sensor signal 17D, 17E, 17F along a bus 29A or otherwise, such as wirelessly, to a controller 16B. The controller 16B is configured with a processor on which an algorithm is stored that processes signals 17D, 17E, 17F and provides a control signal 21B providing level, temperature and/or viscosity information for fluid in the reservoir 15D adjacent each sensor 12D, 2E, 12F to an output device 23B to enable monitoring of the reservoir 15D. A power source 38B which may be a battery, a generator, a solar cell, or other form of power, is operatively connected to the controller 16B for providing power to the controller 16B and through the controller 16B to the sensors 12D, 12E, 12F for energizing the sensors 12D, 12E, 12F. The transfer conductors shown providing the sensor signals 17D, 17E, 17F and providing power from the controller 16B to the sensors 12D, 12E, 12F may be bundled in a unitary bus or otherwise.

Fourth Embodiment of a Fluid Level Detection System

Figure 4A:
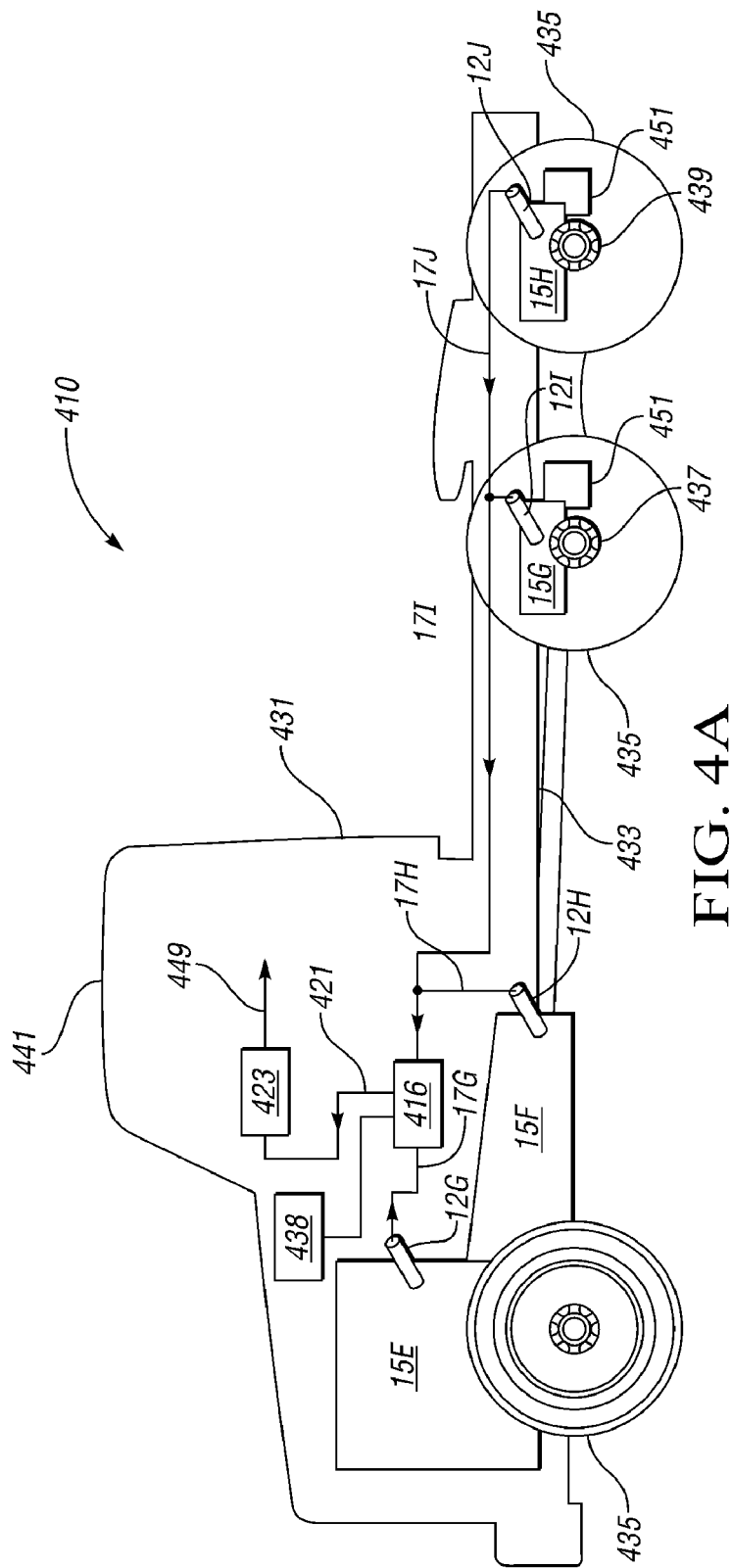
FIG. 4A is a schematic illustration of a vehicle with a fluid level detection system.
Figure 4B:
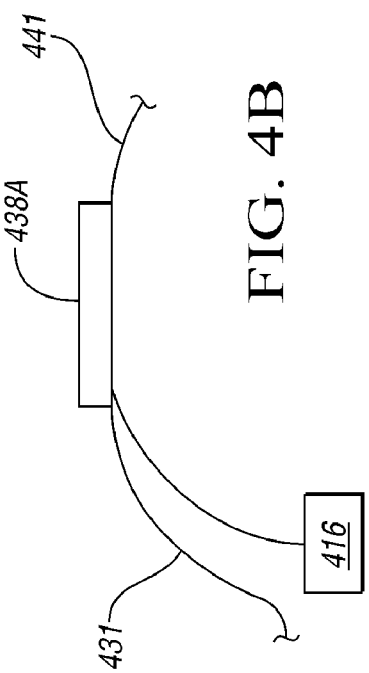
FIG. 4B is a schematic illustration of an alternative power source for the fluid level detection system of FIG. 4A.

Referring to FIG. 4A, a fuel level detection system 410 for a vehicle 431 includes multiple fluid-containing components such as an engine 15E, a transmission 15F, a first axle differential 15G operatively connecting vehicle wheels 435 of a first rear axle 437 and a second axle differential 15H operatively connecting vehicle wheels 435 of a second rear axle 439, all of which are operatively supported by a multi-component vehicle frame 433. The engine 15E and the transmission 15F have on and off states and are subject to circulating fluid creating static and dynamic fluid levels during operation, as described above. The differentials 15G and 15H may experience a dynamic level during vehicle operation, when vehicle wheels 435 are in motion and a static level when the vehicle 431 is at rest. Sensors 12G, 12H, 12I, 12J are mounted to the engine 15E, transmission 15F, and differentials 15G, 15H, respectively. The sensors 12G, 12H, 12I and 12J are configured and operate as described with respect to sensors 12 or 112 of FIGS. 5 and 6. Specifically, the sensors 12G, 12H, 12I and 12J provide sensor signals 17G, 17H, 17I and 17J along transfer conductors to a controller 416. Alternatively, the sensors 12G, 12H, 12I and 12J may communicate with the controller 416 wirelessly. The controller 416 is configured with a processor on which an algorithm is stored. The algorithm processes the sensor signals and provides a control signal 421 along a transfer conductor, or wirelessly, to an output device 423. The control signal 421 is indicative of the various fluid levels within the engine 15E, transmission 15F and differentials 15G, 15H. The output device 423 may be a display on the vehicle instrument panel, an audio signal, or any other indicator. A power source 438, such as a vehicle battery or generator, provides electric power through the controller 416 to the sensors 12G, 12H, 12I and 12J for energizing the sensors 12G, 12H, 12I and 12J. Alternatively, the power source may be a solar panel 438A mounted to a roof 441 of the vehicle 431, as shown in FIG. 4B.

In one embodiment, the output device 423 may be a second controller which controls operation of one or more of the engine 15E, transmission 15F, differentials 15G, 15H and/or a vehicle braking system 451. The output device 423 provides an output signal 449 that is provided to the braking system 451 to slow the vehicle wheels 435. This may occur when the sensor signals 17G, 17H, 17I, 17J indicate that fluid level in one or more of the engine 15E, transmission 15F, or differentials 15G, 15H has reached a low dynamic level at which the vehicle 431 should not be operated at high speeds.

While the best modes for carrying out the invention have been described in detail, those familiar with the art to which this invention relates will recognize various alternative designs and embodiments for practicing the invention within the scope of the appended claims.

The invention claimed is:

1. A fluid level detection system comprising:
a fluid reservoir defining a cavity for holding fluid therein;
a fluid level sensor having a solenoid body mounted to the fluid reservoir with a first portion extending inside of the cavity and a second portion extending outside of the reservoir, a coil, and an armature; wherein the solenoid body defines an armature chamber in which the armature travels in response to energizing of the coil;
a pole piece;
a biasing device biasing the armature away from the pole piece, the biasing device and coil being configured to cycle the armature in the armature chamber as the coil is cyclically energized;
wherein the solenoid body defines a first opening establishing fluid communication between the armature chamber and the cavity defined by the reservoir, travel time of the armature within the armature chamber thereby being affected by fluid level in the reservoir; wherein the sensor is operable to provide a sensor signal indicative of the travel time;
a controller operatively connected to the sensor and operable to receive the sensor signal from the sensor and formulate a control signal corresponding thereto; and
a power source operatively connected to the controller for energizing the coil and the controller.

2. The fluid level detection system of claim 1, further comprising:
an output device operatively connected to the controller and operable to receive the control signal.

3. The fluid level detection system of claim 2, further comprising:
a first cable connecting the sensor with the controller and configured to transfer the sensor signal from the sensor to the controller; and
a second cable connecting the controller with the output device and configured to transfer the control signal from the controller to the output device.

4. The fluid level detection system of claim 2, wherein the output device is configured to provide one of a visual and an audio indicator of fluid level in the reservoir, the indicator being based on the control signal.

5. The fluid level detection system of claim 2, wherein the sensor is a first sensor mounted to the fluid reservoir at a first location and the sensor signal is a first sensor signal; and further comprising:
a second sensor substantially identical to the first sensor and mounted to the fluid reservoir at a second location corresponding with a different fluid level in the reservoir; wherein the controller is operatively connected to the second sensor to receive a second sensor signal therefrom.

6. The fluid level detection system of claim 2, wherein the sensor is a first sensor, the fluid reservoir is a first fluid reservoir, and the sensor signal is a first sensor signal; and further comprising:
a second fluid reservoir;
a second sensor substantially identical to the first sensor and mounted to the second fluid reservoir; and wherein the controller is operatively connected to the second sensor to receive a second sensor signal therefrom and formulate another control signal corresponding thereto.

7. The fluid level detection system of claim 1, wherein the controller is further operable to determine at least one of temperature of the fluid and viscosity of the fluid.

8. The fluid level detection system of claim 1, wherein the power source is one of a battery, a generator and a solar cell.

9. The fluid level detection system of claim 1, wherein the opening is a first opening and establishes fluid communication between a first portion of the armature chamber and the cavity; wherein the solenoid body defines a second opening permitting fluid communication between the cavity and a second portion of the armature chamber, the first and second portions of the armature chamber being at opposing sides of the armature, both sides of the armature thereby being in fluid communication with the fluid reservoir; and
wherein the first opening is in communication with the fluid reservoir at a higher fluid level than the second opening.

10. The fluid level detection system of claim 1, wherein the controller is configured to determine fluid temperature based on electrical resistance of the coil.

11. The fluid level detection system of claim 1, wherein the controller is configured to determine fluid viscosity based on a comparison of armature travel time with predetermined armature travel times associated with predetermined viscosity values.

12. The fluid level detection system of claim 1, wherein the armature travels substantially transverse to fluid level in the reservoir.

13. The fluid level detection system of claim 1, in combination with a fluid-requiring component that is in fluid communication with the reservoir and has an on-state in which fluid flow is dynamic as fluid is provided from the reservoir to the fluid-requiring component, and an off-state in which fluid in the reservoir and the fluid-requiring component is static; wherein a predetermined static fluid level is above the first opening and a predetermined dynamic fluid level is below the first opening.

14. A fluid level detection system for a vehicle having a fluid-containing component, comprising:
a fluid level sensor having a solenoid body mounted to the fluid-containing component with a first portion extending inside of the fluid reservoir and a second portion extending outside of the fluid-containing component, a coil, and an armature; wherein the solenoid body defines an armature chamber in which the armature travels in response to energizing of the coil;
a pole piece;
a biasing device biasing the armature away from the pole piece, the biasing device and coil being configured to cycle the armature in the armature chamber as the coil is cyclically energized;
wherein the solenoid body defines a first opening establishing fluid communication between the armature chamber and the cavity defined by the fluid-containing component, travel time of the armature within the armature chamber thereby being affected by fluid level in the fluid-containing component; wherein the sensor is operable to provide a sensor signal indicative of the travel time;
a controller operatively connected to the sensor and operable to receive the sensor signal from the sensor and formulate a control signal corresponding thereto; and
a power source operatively connected to the controller for energizing the coil and the controller.

15. The fluid level detection system of claim 14, wherein the fluid-containing component is one of a transmission, an engine and a differential.

16. The fluid level detection system of claim 14, wherein the vehicle includes an output device, and further comprising:
a first cable operatively connecting the sensor and the controller and operable to transmit the sensor signal to the controller; and
a second cable operatively connecting the controller with the output device and operable to transmit the control signal to the output device.

17. The fluid level detection system of claim 14, wherein the controller is a first controller; wherein the vehicle includes a second controller; and wherein the output device is the second controller.

18. The fluid level detection system of claim 17, wherein the vehicle has wheels; wherein the second controller is operatively connected with the wheels and is operable for providing an output signal in response to the control signal; and wherein the output signal is operable for slowing the wheels.

19. The fluid level detection system of claim 14, wherein the vehicle has at least one of a battery and a generator, and wherein the power source is the at least one of a battery and a generator.

20. The fluid level detection system of claim 14, wherein the opening is a first opening and establishes fluid communication between a first portion of the armature chamber and the cavity; wherein the solenoid body defines a second opening permitting fluid communication between the cavity and a second portion of the armature chamber, the first and second portions of the armature chamber being at opposing sides of the armature, both sides of the armature thereby being in fluid communication with the fluid-containing component; and
wherein the first opening is in communication with the fluid-containing component at a higher fluid level than the second opening.

* * * * *